United States Patent [19]
Eng et al.

[11] Patent Number: 5,441,722
[45] Date of Patent: Aug. 15, 1995

[54] SHORT SYNTHESIS OF 5,6-DIHYDRO-(S)-4-(ETHYLAMINO)-(S)-6-[C³H₃]-4H-THIENO[2,3-B]THIOPYRAN-2-SULFONAMIDE 7,7-DIOXIDE AND RELATED NON RADIOACTIVE COMPOUNDS

[75] Inventors: Wai-Si Eng, Maple Glen; Donald H. Burns, Harleysville; Gerald S. Ponticello, Lansdale; Harold G. Selnick, Ambler, all of Pa.

[73] Assignee: Merck & Co., Inc., Rahway, N.J.

[21] Appl. No.: 198,248

[22] Filed: Feb. 18, 1994

[51] Int. Cl.$^6$ .................... A61K 51/04; A61K 31/38; C07D 495/02
[52] U.S. Cl. .................... 424/111; 514/432; 514/444; 549/23; 549/53
[58] Field of Search .................... 549/23, 66, 53; 514/432, 444, 445, 446

[56] References Cited

U.S. PATENT DOCUMENTS

| | | | |
|---|---|---|---|
| 4,968,815 | 11/1990 | Blacklock et al. | 549/66 |
| 5,157,129 | 10/1992 | Blacklock et al. | 549/23 |

*Primary Examiner*—Shean Wu
*Attorney, Agent, or Firm*—Sylvia A. Ayler; Mark R. Daniel

[57] ABSTRACT

This invention concerns the short synthesis of 5,6-dihydro-(S)-4-(ethylamino)-(S)-6-[C³H₃]-4H-thieno [2,3-b]thiopyran-2-sulfonamide 7,7-dioxide and related non-radioactive and radioactive compounds. The key step is the regioselective and stereo-controlled methylation of the C-6 (α-sulfone) carbanion in the presence of the monoprotected sulfonamide anion.

9 Claims, No Drawings

SHORT SYNTHESIS OF 5,6-DIHYDRO-(S)-4-(ETHYLAMINO)-(S)-6-[$C^3H_3$]-4H-THIENO[2,3-B]THIOPYRAN-2-SULFONAMIDE 7,7-DIOXIDE AND RELATED NON RADIOACTIVE COMPOUNDS

BACKGROUND OF THE INVENTION

The current therapy for control of elevated intraocular pressure (IOP) or ocular hypertension which is believed to be a factor in the onset and progress of glaucoma is typically effected with a variety of topically applied agents which fall within four categories: β-blockers, sympathomimetic agents, parasympathomimetic agents and cholinesterase inhibitors. The adjuvant oral administration of a carbonic anhydrase inhibitor (CAI) is practiced when the above-described topical agent's side effect limits its use and/or it fails to achieve adequate IOP control. The orally active CAI's can exhibit serious side-effects such as anorexia, gastrointestinal upset and parasthesias. Therefore, an intense and ongoing search has been mounted for a topically active CAI that would not exhibit such side effects due to the route of administration and inherent target organ specificity. This search has resulted in the discovery of a class of compounds by Baldwin et al (U.S. Pat. No. 4,797,413; incorporated herein by reference) of general formula:

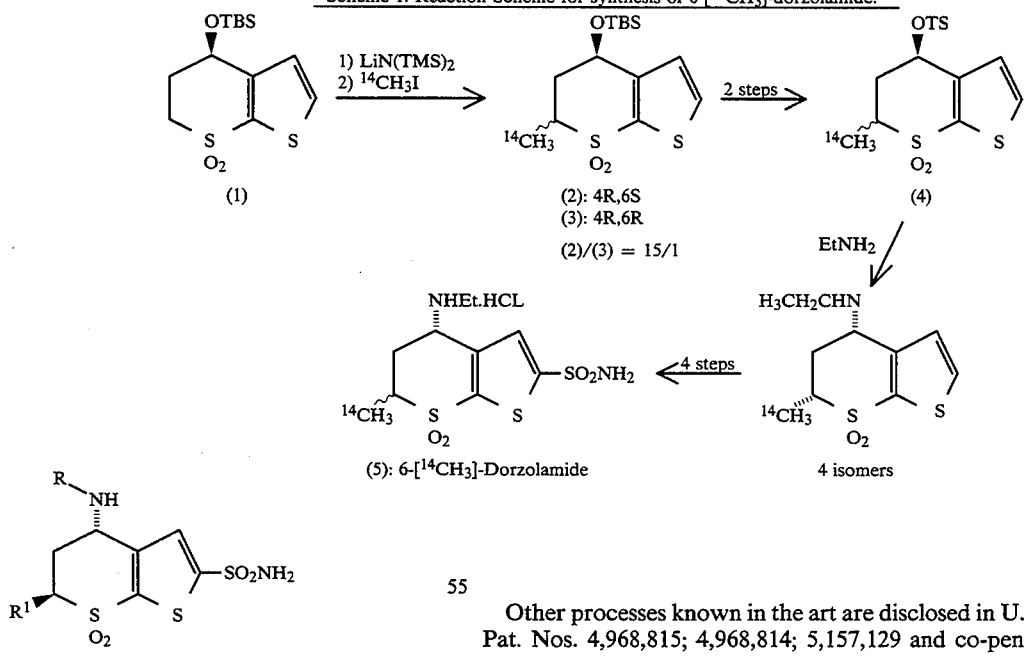

wherein R and $R^1$ are lower alkyl, especially dorzolamide, wherein R is ethyl and $R^1$ is methyl. Additionally, radioisotopically labeled dorzolamide type compounds at the 6-methyl position (6-[$^{14}CH_3$]-analogs) are disclosed in Dean D.C., et al., Synthesis and Application of Isotopially Labelled Compounds (1991). The compounds are effective for the treatment of elevated intraocular pressure.

The process for making the 6-[$^{14}CH_3$]-dorzolamide type compounds teaches an eight step sequence wherein a specific activity of 26.3 mCi/mmol is obtained from a homochiral cyclic sulfone intermediate. As shown in Scheme 1, diastereoselective methylation with [$^{14}C$]methyl iodide of an enantiomerically enriched (4R), t-butyldimethylsilyl protected alcohol (1) produced a 15:1 mixture of the 4R,6S::4R,6R diastereomers e2 and 3) in near quantitative yield. While this asymmectric alkylation provides an entry to the desired radiotracer, the inherent low specific activity of $^{14}C$-labeled radiotracers (only ca. 60 mCi/mmol for one $^{14}C$ atom per label compound molecule) is inadequate for some biological reactions and biochemical studies.

The instant process results in the sysnthesis of a 6-[$C^3H_3$]-dorzolamide with a specific activity 2000 fold higher than the [$^{14}C$]dorzolamide. Additionally, in the $^{14}C$-sequence the functional group elaborations after the methylation are lengthy and involve procedures which are not easily amenable to use in a sub-milligram scale radiolabeling with other radiotracers such as tritium. Moreover, the instant process (see Scheme 2 below) is unlike the radiosynthesis of the [$^{14}C$]dorzolamide (Scheme 1), in which the creation of both chiral centers and sophisticated separations of the resulting four isomers were involved. The instant synthesis of 6-[$C^3H_3$]-dorzolamide starts with an optically enriched 4S-ethylamino precursor (6 of Scheme 2). This allows the methylated, diastereomeric products to be easily purified with conventional high performance liquid chromatography (HPLC) to afford the instant 6-[$C^3H_3$]-dorzolamide (10) in high optical purity as well as its 4S, 6R isomer.

Other processes known in the art are disclosed in U.S. Pat. Nos. 4,968,815; 4,968,814; 5,157,129 and co-pending U.S. application No. 08/035,523. However, these processes involve procedures that are not easily amenable for the preparation of 6-[$C^3H_3$]-dorzolamide, especially at the no-carder-added scale. Compared with all the above-mentioned processes, the present invention offers a shorter and more advantageous approach to prepare high specific activity 6-[$C^3H_3$]-dorzolamide and is more practical at the no-carder-added scale. It also offers an alternative approach for the preparation of carbonic anhydrase inhibitors described in U.S. Pat. No. 4,797,413 and the corresponding 6R-isomers.

SUMMARY OF THE INVENTION

This invention is concerned with the preparation of the radioactive product 6-[C³H₃]-dorzolamide and the corresponding 6R-isomer via a two-step radiosynthetic process. The key step in this novel process is the regioselective and stereo-controlled methylation of the C-6 (α-sulfone) carbanion in the presence of the mono-protected sulfonamide anion. The 6R-isomer is the major product of the process while the minor product of the process, 6-[C³H₃]-dorzolamide, is obtained in high specific activity and high enantiomeric purtiy through chromatographic purification.

DETAILED DESCRIPTION OF THE INVENTION

The novel process of the present invention can be depicted as shown in Scheme 2:

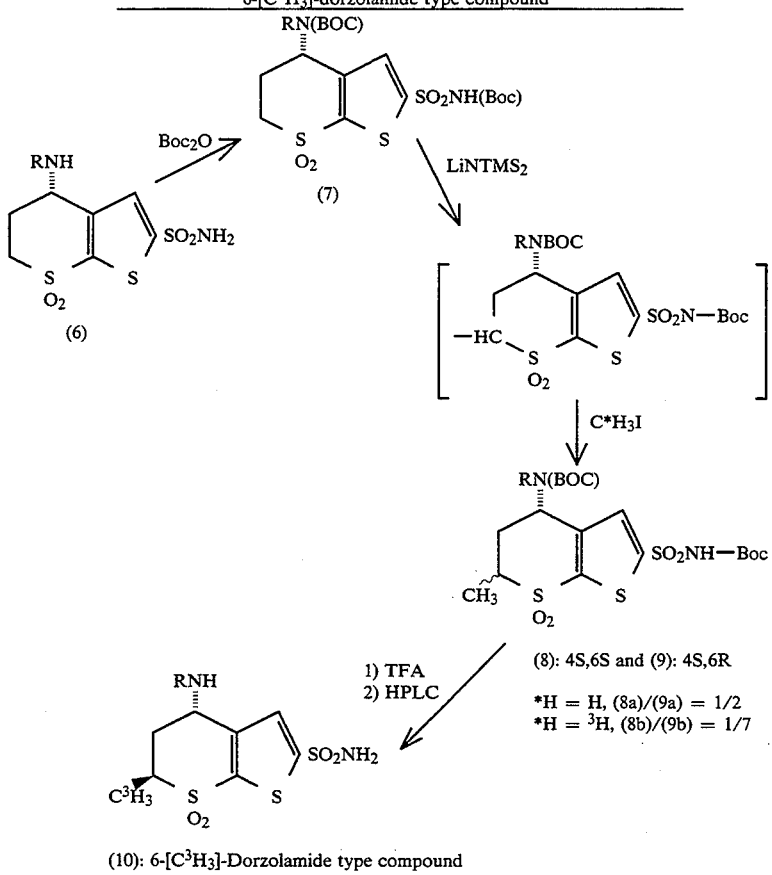

Scheme 2. Reaction Scheme for synthesis of high specific activity 6-[C³H₃]-dorzolamide type compound (10): 6-[C³H₃]-Dorzolamide type compound wherein R is as described above.

The short radiosynthesis of 6-[C³H₃]-dorzolamide (10) and the radioinert isomers thereof starts with the optically enriched chiral 4S-ethylamino precursor, desmethyldorzolamide (6). The key feature of this process is the regioselective and stereo-controlled methylation of the C-6 (α-sulfone) carbanion. To direct the methylation exclusively to C-6, the nitrogens of the amine and sulfonamide moieties are protected using protecting groups such as t-Butoxycarbonyl (Boc), carbobenzyloxy (CBz) and the like. The process comprises mixing desmethyldorzolamide (6) with from about 4 to about 8 equivalents (eqs) of di-t-butyl dicarbonate, carbobenzyloxy chloride and the like, which are commercially available, preferrably di-t-butyl dicarbonate, in the presence of about 2 to about 3 equivalent (eq) (each) of Et₃N/DMAP at a temperature of −78° C. to 30° C. and stirring at room temperature for about 0.1 to 100 hours until the reaction is complete. The solvents are then removed in vacuo and the residue purified with standard chromatographic procedures known in the art such as silica gel flash chromatography to give the N, N'-diBoc-derivative (7) in about 10 to about 50% yield. As a result, the secondary amine in (7) is completely protected while the mono-N-Boc-protected sulfonamide is electronically and sterically deactivated enough to decrease the chances of forming the corresponding N-alkylation product. Such sulfonamide-methylated by-products, which are easily identifiable by NMR: δ∼3ppm NCH₃, are unexpected even under conditions where excess base and methyl iodide were used. The use of Boc-protected sulfonamides in organic synthesis is discussed in Loev B., et al., Chemistry and Industry 20:973 (1968); and Wang H. and Hu S., J. Taiwan Pharm. Assoc. 39:92 (1987).

The success of the instant process also requires that the stereochemistry at C-4 not be lost due to base catalyzed epimerization of the ethylamino substiment. This type of epimerization has been reported on acyl-derivatized analogs of dorzolamide when the acylamine is heated for an extended time in the presence of excess base (see U.S. Pat. No. 5,011,942). However, since the generation of the carbanion and subsequent methylation proceed rapidly and at a very low temperature of about −100° C. to about −50° C., epimerization with the instant process is substantially non-existent as evidenced by the high enantiomeric excess (>98.4%) of the final 6-[$C^3H_3$]-dorzolamide product, discussed in detail below.

A cooled solution of N, N'-diBoc-derivative (7) in a solvent such as anhydrous tetrahydrofuran (THF), ether, dioxane, and the like, is then treated with a slight excess from about 2.0 eq to about 3.0 eq of a base belonging to the group consisting of lithium bis(trimethylsilyl)amide, n-butyl lithim, tert-butyl lithium, or lithium diisopropylamide, preferrably lithium bis(trimethylsilyl)amide, and the solution stirred at about −100° C. to about −50° C. for about 1 to about 30 minutes. The solution is further slowly treated with from about 0.5 eq to about 1.5 eq, of an alkylhalide such as methyl iodide, ethyl iodide, propyl iodide and the like, preferably methyl iodide, which is dissolved in from about 0.01 to about 1.0 mL of a solvent such as THF, ether, dioxane, and the like and the resulting mixture is stirred at about −78° C. to about 30° C. for about 1 to about 10 hours, to give a mixture of C-6 methylated isomers (8) and (9). The reaction is quenched by the addition of wet ether at about −78° C. to about 30° C., followed by a concentration of the solution in vacuo. The yield of the two methylated products was from about 15 to about 35% with a ratio of 6R:6S (9a:8a) equaling 2:1 as determined by NMR analysis of the crude reaction mixture.

The above procedure can also be modified to incorporate a radio-labeled side chain in the 6-position. Such a radio-alkylation comprises dissolving N, N'-diBoc-derivative (7) in a solvent such as anhydrous tetrahydrofuran (THF), removing the solvent in vacuo and drying the residue under high vacuum while allowing the residue to warm to a temperature of about 20° C. to about 40° C. The dried residue is redissolved in anhydrous THF, ether, dioxane and the like under an inert gas, such as argon, helium and the like and cooled to a temperature of about −100° C. to about −50° C. Lithium bis(trimethylsilyl)amide, from about 2.0 eq to about 3.0 eq is then slowly added, the mixture is stirred from about 1 to about 120 minutes and then frozen to about below −110° C. Freshly generated radiolabeled alkylhalide such as methyl halide, ethyl halide, propyl halide and the like, preferably $C^3H_3I$ (specific acitivity: ca. 80 Ci/mmol), from about 0.5 eq to about 1.0 eq is added to the frozen mixture via vacuum transfer, the resulting mixture is allowed to warm to a temperature of about −75° to about −80° C. and stirred at that temperature for about 1 to about 10 hours. The reaction is quenched at about −50° C. to about −80° C. by the addition of wet ether or like solvent. Volatiles are removed in vacuo and the residue redissolved in an alcohol such as ethanol, methanol and the like. HPLC analysis of the mixture revealed a methylation yield of ca. 20 to 40% (based on the absorbance of the unreacted precursor, k'=1.7 and that of 8b and 9b, k'=2). The limited amount of alkylhalide employed is essential to make full use of the radioisotope source, as well as to prevent the formation of the C-6 dimethylated by-product. The two methylated products have a ratio of 6R:6S (9b:8b) equaling 7:1.

The two methylated products (8) and (9) are then deprotected by any means known to those skilled in the art. For example, the unpurified mixture of the tritium-methylated diastereomers (8b) and (9b) is concentrated in vacuo, treated with from about 1eq to about 1000eq TFA and then stirred at room temperature from 12 to 48 hours. The resulting mixture is then concentrated in vacuo and purified. Deprotecting with TFA offers a convenient sample preparation for the final HPLC purification, since TFA can be simply removed in vacuo.

Initial HPLC purification can be performed by any suitable method known in the art, such as on a semi-preparative, reverse phase column to remove the majority of the unreacted desmethyl precursor and the 4S, 6R products. The fractions containing the radiotracer (10) can then be further HPLC purified resulting in >99% of 4S,6S [$C^3H_3$]-dorzolamide (10) isomer, with a high specific activity (>74 Ci/mmol) as determined by UV analysis of the final fraction against a standard curve established with radioinert dorzolamide. No unreacted, radioinert desmethyldorzolamide (7) was found in the final fraction. The optical purity of 6-[$C^3H_3$]-dorzolamide was determined with chiral HPLC to be >99.2% (approaching detection limit), which corresponds to >98.4% e.e.

Instead of a two pot process, the instant radiochemical synthesis can be carried out wherein the alkylation and subsequent deprotection step occur in the same reaction vessel to reduce the number of manipulations involving radioactive compounds. The instant short synthetic sequence can also be applied in radiotracer synthesis involving short-lived isotopes, such as methylation with [$^{11}C$]methyliodide, as well as the incorporation of radiotraced $C^1$ to $C^3$ side chains in the 6-positions.

PROCEDURE

Unless otherwise mentioned, solvents and reagents were purchased from either Aldrich-Sigma or Fisher Scientific. $^1H$ NMR spectra were obtained in a Varian Infinity-300 spectrometer in $CDCl_3$ with TMS ($\alpha$-O ppm) as an internal standard. High performance liquid chromatography (HPLC) analysis of radioinert compounds were performed on a system consisting of a Waters 600E gradient pump, a Rheodyne injector, and either a $C^{18}$ $\mu$-Bondapak reverse phase column (4mm×25cm), a Vydac $C_{18}$ peptide protein column (4mm×25 cm), or a Zorbax RX-$C_8$ colunto (4mm×15 cm) for reverse phase HPLC and a Chromtech Chiral-AGP column (4mm×10cm) for chiral HPLC. The pump and UV detecton and data processing with a Waters 991 diode array detector were controlled via a Powefiine ™ package. HPLC analyses and preparations of radioactive compounds were performed on a similar system with the exception that the on-line detection results from a Beckman 171 HPLC radioactivity detector were also collected and processed. Preparative HPLC purifications were performed on an Alltech $C_{18}$ Econosil semi-preparative column (10mm×25 cm). Sample radioactivities were determined on a LKB Wallac $^{14}$ $^{10}$ scintillation counter and UV measurements were performed on a HP-8452A diode array spectrophotometer.

Synthesis

N,N'-Di(t-butoxycarbonyl)-5,6-dihydro-4H-(S)-4-ethylaminothieno-[2,3-b]-thiopyran-2-sulfonamide-7,7-dioxide(7).

The HCL salt of 6-desmethyldorzolamide 6, $\alpha$=34.6°, e.e.>99%, 300 mg, 1.1 mmol) was mixed with $Et_3N$ (240 mg, 2.2 mmol) and the mixture was dissolved in 2 mL of dry $CH_2Cl^2$. Into the solution was added DMAP (260 mg, 2.2 mmol), followed by di-t-butyl dicarbonate (500 mg, excess) in batches (gas generated).

The resulting yellow solution was stirred at room temperature for 72 hours. The solvents were removed in vacuo and the residue was purified with silica gel flash chromatography (0–100% ethyl acetate/hexane) and 105 mg of purified (7) was obtained (0.22 mmol, 20% yield).

N,N'-Di(t-butoxycarbonyl)-5,6-dihydro-4H-4-ethylamino-6-methylthien[2,3-b]-thiopyran-2-sulfonamide-(7,7)-dioxide (8a and 9b)

To a dry ice cooled solution of 7, (17 mg, 0.036 mmol) in 1 mL of anhydrous THF was added dropwise 0.11 mL of lithium bis(trimethylsilyl)amide (1 M in THF, 0.11 mmol). The bright yellow solution was stirred at −78° C. for 20 minutes before a solution of methyl iodide (5 mg, 0.033 mmol) in THF (anhydrous, approx. 0.2 mL) was added dropwise. The resulting mixture was further stirred at −78° C. for 4 hours and then was quenched by the addition of 1 mL of wet ether (ether treated with $NH_4Cl$-saturated water solution) at −78° C. The mixture was then concentrated in vacuo and analyzed by NMR. The resonance of the thiophene protons (7:δ=7.64 ppm, 8a: 7.75 and 9a: 7.55) were indicative of the reaction progress, which revealed that while the total methylation yield approached ca. 20–30% with very few byproducts the 6R:6S product ratio (9a:8a) was approximately 2:1, favoring the 6R methylated product (9a). The identity of the two isomers was confirmed by a comparision with the products of independent syntheses from the authentic dorzolamide and its 6R isomer using a procedure similar to that described for ().

N,N'-Di(t-butoxycarbonyl)-5,6-dihydro-4H-4-ethylamino-6-[$^3H_3$-methyl]-methylthieno [2,3-b]-thiopyran-2-sulfonamide-7,7-dioxide (8b and 9b)

Into several milliliters of anhydrous THF in a 10 mL reaction flask was dissolved 7, (35 mg, 0.073 mmol). The solvent was then removed in vacuo, and the residue dried under high vacuum with warming to 35° C. The dried residue was redissolved in 2 mL of anhydrous THF under Ar and cooled to −78° C. To the solution was added dropwise 0.22 mL of lithium bis(trimethylsilyl)amide (1 M in THF, 0.22 mmol) and the mixture stirred for 10 minutes, after which it was frozen. Freshly generated $C^3H_3I$ (0.07 mmol, specific activity: ca. 80 Ci/mmol) was added to the reaction flask via vacuum transfer. The resulting mixture was allowed to warm to −78° C. and stirred at that temperature for 4 hours. The reaction was quenched at −78° C. by the addition of 1 mL of wet ether (treated with $NH_4Cl$-samrated water solution). Volatiles were removed in vacuo and the residue redissolved in EtOH. A total of ca. 500 mCi of radioactivity was recovered. HPLC analysis (Zorbax Rx-$C^8$, 60% $CH_3CN$/1% TEAOAC buffer, pH=4, 1 mL/min, UV 254nm) of the resulting mixture revealed that the methylation yield was ca. 35% (based on the absorbence of the unreacted precursor, k'=1.7 and that of 8a and 9a, k'=2). TLC analysis ($SiO_2$, G, 60% ethyl acetate/hexane) of the mixture showed three radioactive peaks: 5% at the origin, 83% at R$_f$0.24 9(9b), and 12% at R$_f$0.32 (8b). This corresponded to a 9b:8bnratio of 7:1.

5,6-dihydro-4H-(S)4-ethylamino-(S)-6-[$^3H_3$-methyl]-methylthieno[2,3-b]-thiopyran-2-sulfonamide-7,7-dioxide (6-[$CH_3$]-dorzolmide, 10)

A fraction (30 mCi) of the mixture of (8b and 9b) was concentrated in vacuo and 1 mL of TFA was added to the residue. The resulting solution was stirred overnight at room temperature. The resulting mixture was concentrated in vacuo and first purified with an Alltech semiprep HPLC column (15% $CH_3CN$/$H_2O$, both containing 0.1% TFA, 1.5 mL/min). The fraction containing the desired 4S, 6S isomer (10) was collected and further purified with a Vydac $C^{18}$ column (6% $CH_3CN$/$H_2O$, both containing 0.1% TFA, 1 mL/min). Thus, a fraction (ca. 1.5 mCi) was obtained, the HPLC analysis of which (Vydac $C^{18}$, 6% $CH_3CN$/$H_2O$, both containing 0.1% TFA, 1 mL/min) revealed >99% of the desired radiotracer (10, k'=w.14) and <1% of its 4S,6R isomer (k'=2.57) and other radioactive impurities. No unreacted desmethyldorzolamide (2, k'=1.29) was detected (UV detection limit well below 1%). The optical purity of the fraction was determined by chiral HPLC (Chiral-AGP, 0.5 mL/min, 100% 0.1 M phosphate buffer, pH$_7$) and found to comain >99.2% of 4S,6S isomer (10, k'=4.7) and <0.8% of its 4S,6R isomer (k'=5.75). The specific activity of the radiotracer (10) was found to be >74 Ci/mmol, based on the radioactivity and the mass, determined by UV analysis (254nm) against a standard curve established with radioinert dorzolamide, of the final product (10).

What is claimed is:

1. A process for the preparation of a Compound of structural formula I:

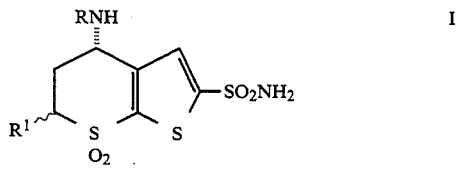

and its hydrochloride salt wherein R is $C^1$–$C^3$ alkyl and $R^1$ is $C^1$–$C^3$ alkyl or a radio-labeled $C^1$–$C^3$, which comprises the steps of:

A) protecting the nitrogen substituents of a compound of structual formula II

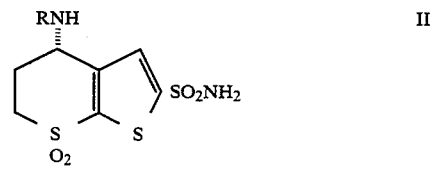

by treating the compound of structual formula II with an excess of a blocking agent from about 4 eq to about 8 eq, belonging to a group consisting of di-t-butyl dicarbonate, or carbobenzyloxy chloride or in the presence of from about 2 eq to about 3 eq (each) $Et_3N$/DMAP to form a compound of structural formula HI:

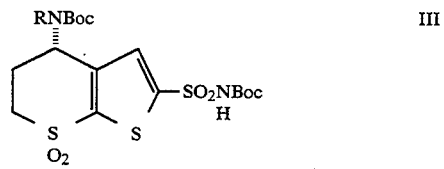

B) methylating the compound of structural formula III at the C-6 position, treating the compound of structural formula III with an excess of a base, from about 2.0 eq to about 3.0 eq, selected from the group consisting of lithium bis(trimethylsilyl)amide, n-butyl lithium, tert-butyl lithium, or lithium diisopropylamide in the presence of an anhydrous solvent selected from the group consisting of THF, ether, or dioxane, and adding from about 0.5 eq to about 1.5 eq of methyl iodide in the presence of an anhydrous THF to form a compound of Structural formula IV:

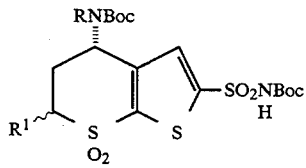

C) deprotecting the nitrogen substituents of the compound of structural formula IV, and purifying and isolating the compound of structural formula I, wherein R and $R^1$ are as above.

2. The process of claim 1, wherein R is ethyl and $R^1$ is is methyl.

3. The process of claim 1, wherein R is ethyl and the radio-labeled $C^1$–$C^3$ alkyl of $R^1$ is $^3H$, $^{14}C$ or $^{11}C$.

4. The process of claim 1, wherein R is ethyl and $R^1$ is $C^3H_3$.

5. The process of claim 1, wherein the blocking agent is di-t-butyl dicarbonate and the base is lithium bis(trimethylsilyl)amide.

6. A compound of the formula:

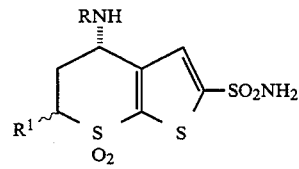

wherein R is C1–3 alkyl and $R^1$ is a radio-labeled $C^1$–$C^3$ alkyl belonging to the group consisting of $^3H$ or $^{11}C$.

7. A compound according to claim 6 wherein R is ethyl.

8. A compound according to claim 6 wherein the R is ethyl and $R^1$ is $C^3H_3$.

9. The process of claim 1, wherein the methylation and deprotection occurs in the same reaction vessel.

* * * * *

UNITED STATES PATENT AND TRADEMARK OFFICE
CERTIFICATE OF CORRECTION

PATENT NO. : 5,441,722
DATED : August 15, 1995
INVENTOR(S) : Eng et al

It is certified that error appears in the above-indentified patent and that said Letters Patent is hereby corrected as shown below:

Col. 8, Claim 1, line 54, delete "HI" and insert in its place -- III --.

Signed and Sealed this

Twelfth Day of December, 1995

Attest:

BRUCE LEHMAN

Attesting Officer

Commissioner of Patents and Trademarks